US008271081B2

(12) United States Patent
Hauck et al.

(10) Patent No.: US 8,271,081 B2
(45) Date of Patent: Sep. 18, 2012

(54) SYSTEMS AND METHODS FOR USE WITH AN IMPLANTABLE MEDICAL DEVICE FOR DISCRIMINATING VT AND SVT BE SELECTIVELY ADJUSTING ATRIAL CHANNEL SENSING PARAMETERS

(75) Inventors: Gregory Hauck, Valencia, CA (US); Martin Cholette, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 343 days.

(21) Appl. No.: 12/778,499

(22) Filed: May 12, 2010

(65) Prior Publication Data

US 2011/0282405 A1    Nov. 17, 2011

(51) Int. Cl.
*A61N 1/365* (2006.01)

(52) U.S. Cl. .................... 607/4; 607/5; 607/14

(58) Field of Classification Search .................. None
See application file for complete search history.

(56) References Cited

U.S. PATENT DOCUMENTS

| | | |
|---|---|---|
| 5,240,009 A | 8/1993 | Williams |
| 5,273,049 A | 12/1993 | Steinhaus et al. |
| 5,779,645 A | 7/1998 | Olson et al. |
| 6,512,952 B2 | 1/2003 | Stahmann et al. |
| 6,516,219 B1 | 2/2003 | Street |
| 6,628,988 B2 | 9/2003 | Kramer et al. |
| 6,636,764 B1 | 10/2003 | Fain et al. |
| 6,643,546 B2 | 11/2003 | Mathis et al. |
| 6,907,286 B1 | 6/2005 | Kroll et al. |
| 7,058,450 B2 | 6/2006 | Struble et al. |
| 7,191,002 B1 | 3/2007 | Kroll et al. |
| 7,245,967 B1 | 7/2007 | Shelchuk |
| 7,295,873 B1 | 11/2007 | Min et al. |
| 7,398,123 B1 | 7/2008 | Levine |
| 8,055,342 B2 * | 11/2011 | Zhang et al. .................. 607/28 |
| 2007/0179390 A1 | 8/2007 | Schecter |
| 2008/0161870 A1* | 7/2008 | Gunderson ...................... 607/5 |
| 2008/0306567 A1 | 12/2008 | Park et al. |

* cited by examiner

*Primary Examiner* — Carl H Layno
*Assistant Examiner* — Paula J Stice

(57) ABSTRACT

Techniques are described for discriminating ventricular tachycardia (VT) from supraventricular tachycardia (SVT) in circumstances when the ventricular rate exceeds the atrial rate (i.e. V>A). In one example, an initial atrial rate is detected while employing adjustable atrial channel detection parameters that can affect the detection of the true atrial rate—such as a post-ventricular atrial blanking (PVAB) interval or an atrial channel sensitivity level. If the ventricular rate exceeds a VT rate zone threshold with V>A, the device does not immediately deliver high voltage shock therapy as done in other devices. Rather, the device instead selectively adjusts the atrial channel detection parameter(s) to determine if the true atrial rate is equal to the ventricular rate. If so, then such is an indication that the arrhythmia might be SVT rather than VT and various discrimination procedures are employed to distinguish SVT from VT before therapy is delivered.

17 Claims, 6 Drawing Sheets

SYSTEMS AND METHODS FOR USE WITH AN IMPLANTABLE MEDICAL DEVICE FOR DISCRIMINATING VT AND SVT BE SELECTIVELY ADJUSTING ATRIAL CHANNEL SENSING PARAMETERS

FIELD OF THE INVENTION

The invention generally relates to implantable cardiac stimulation devices, such as pacemakers, implantable cardioverter/defibrillators (ICDs) or cardiac resynchronization therapy defibrillators (CRT-Ds) and, in particular, to techniques for discriminating ventricular tachycardia (VT) from supraventricular tachycardia (SVT) using such devices.

BACKGROUND OF THE INVENTION

A pacemaker is a medical device for implant within a patient that recognizes various arrhythmias such as tachycardia and delivers pacing therapy to the heart in an effort to remedy the arrhythmia. An ICD is a device, also for implant within a patient, which additionally recognizes atrial fibrillation (AF), VT or ventricular fibrillation (VF) and delivers various high voltage electrical shocks to terminate the tachycardia or fibrillation. Within pacemakers and ICDs, it is important to distinguish a tachycardia that arises in the ventricles from those that arise elsewhere in the heart. A tachycardia that arises in the ventricles (referred to as VT) is often more serious than a tachycardia arising elsewhere in the heart, since VT can sometimes lead to VF, which is fatal if untreated. Moreover, the type of therapy to be delivered to the heart depends upon the source of the tachycardia. In particular, it is important to discriminate SVT from VT. SVT is a tachyarrhythmia whose origin is above the ventricles but which is conducted into the ventricles, resulting in an unacceptably rapid ventricular rate. The true underlying arrhythmia in these cases may be, for example, AF, sinus tachycardia (ST), ectopic atrial tachycardia, atrial reentry tachycardia, atrioventricular (A/V) nodal reentry tachycardia, paroxysmal AF or atrial flutter.

Failure to distinguish SVT from VT can result in delivery of inappropriate therapy. Depending upon the capabilities of the implanted device, inappropriate therapy might include the delivery of unnecessary anti-tachycardia pacing (ATP) or the delivery of unneeded high voltage cardioversion shocks. Misidentification of SVT and VT is one of the leading causes of improper device therapy, resulting in the delivery of painful and unnecessary cardioversion shocks.

In particular, problems can arise in devices that automatically deliver high voltage shocks whenever the ventricular rate exceeds a VT rate zone threshold while the observed atrial rate is less than the ventricular rate. In this case, no additional discrimination is ordinarily applied and the arrhythmia is immediately diagnosed as VT with ensuing high voltage therapy. The rationale behind this behavior is that, physiologically, all ventricular tachyarrhythmias where the true ventricular rate exceeds the true atrial rate are considered to be VT. Although this is generally true from a physiological standpoint, there are circumstances of abnormal device behavior that can lead to false VT detections and hence to inappropriate high voltage therapy. For example, the true atrial rate of the patient might be the same as the ventricular rate, but the atrial rate is not properly tracked by the device and is instead underestimated, leading to the false conclusion that the ventricular rate exceeds the atrial rate, with high voltage VT therapy then unnecessarily delivered. These inappropriate shock therapies can significantly affect the quality of life of ICD patients, as well as their morbidity and mortality. Accordingly, reducing inappropriate high voltage shocks that arise in these circumstances is an important problem to solve for patient well being and the invention is generally directed to this end.

SUMMARY OF THE INVENTION

In accordance with an exemplary embodiment of the invention, a method is provided for use by an implantable medical device for distinguishing VT from SVT in circumstances when the ventricular rate exceeds the atrial rate (i.e. V>A). Briefly, an initial atrial rate is detected within the patient while employing at least one adjustable atrial channel detection parameter that can affect the detection of the true atrial rate—such as a post-ventricular atrial blanking (PVAB) interval or an atrial channel sensitivity level. The ventricular rate is also detected and a possible VT is identified based on the ventricular rate. If the ventricular rate exceeds the initial atrial rate while VT is indicated (based, e.g., on the ventricular rate exceeding a VT rate zone threshold), the device does not immediately deliver high voltage shock therapy. Rather, the device instead selectively adjusts the atrial channel detection parameter to determine if the new adjusted atrial rate is substantially equal to the ventricular rate. If so, then such is an indication that the arrhythmia might be SVT rather than VT and so various discrimination procedures are employed to distinguish SVT from VT before therapy is delivered.

In one example, the duration of the PVAB interval is selectively and incrementally decreased to reveal additional high rate atrial events (P-waves) that might have been blanked by the PVAB causing significant underestimation of the true atrial rate. Additionally or alternatively, the atrial channel sensitivity can be selectively and incrementally increased to reveal additional low-magnitude atrial events that might have been overlooked, likewise causing significant underestimation of the true atrial rate. In any case, if the adjusted atrial rate is now found to be substantially equal to the ventricular rate, then the possible VT might instead be SVT and so the device takes steps to distinguish or discriminate VT from SVT based on newly detected atrial and ventricular events. This discrimination can include morphological analysis of ventricular events, as well as an assessment of atrioventricular (AV) association stability. If the discrimination confirms that the arrhythmia is indeed VT, high voltage therapy is promptly delivered. Conversely, if the arrhythmia is found to be SVT, then SVT therapy can be delivered. Preferably, if a series of adjustments to the atrial channel detection parameter(s) do not serve to yield an adjusted atrial rate that is substantially equal to the ventricular rate, the adjustments are stopped and VT therapy is promptly delivered. This helps ensure that therapy is not unduly delayed.

In a first illustrative implementation of the invention, the atrial channel parameter selectively adjusted is the PVAB. The PVAB interval (which can also be referred to as an absolute refractory period) is primarily provided to prevent the device from erroneously responding to far-field R-waves (FFRWs) on the atrial channel but can interfere with the detection of high rate atrial events (i.e. P-waves), particularly during SVT. As such, even if the true atrial and ventricular rates are the same (indicative of a likely SVT), the device might improperly detect a ventricular rate that is greater than the observed atrial rate, triggering inappropriate VT therapy. In particular, if the true atrial and ventricular rates are the same, blanking by the PVAB can result in a detected ventricular rate that is two or three times the detected atrial rate. Accordingly, before reducing the duration of the PVAB, the device preferably ascertains whether the ventricular rate is a whole number multiple of the atrial rate. Incremental adjustments to the PVAB are only made if the ventricular rate is found to be a whole number multiple of the atrial rate; otherwise VT is assumed and VT therapy is promptly delivered. Assuming, though, that the ventricular rate is a whole number multiple of the atrial rate, the PVAB is incrementally decreased by, e.g., 5 milliseconds every N cardiac cycles, where N is programmable. At each new PVAB duration, the device assesses the new (adjusted) atrial rate and compares it with the current ventricular rate to determine if the two rates are now the same (i.e. the device determines if the shorter PVAB reveals a true atrial rate that is actually equal to the ventricular rate.)

Continuing with the first illustrative implementation, if the adjusted atrial rate at the shorter PVAB duration is found to be same as the ventricular rate (i.e. V=A), then the arrhythmia might be SVT rather than VT and so the device takes steps to discriminate the two arrhythmias. First, the device assesses AV association stability, i.e. the device determines whether intrinsic AV conduction delay values are substantially uniform, which would indicate that the high rate ventricular events are correlated with the high rate atrial events, suggesting that the arrhythmia is supraventricular in origin. Second, the device examines the morphology of ventricular events (i.e. QRS complexes, which are also referred to herein as R-waves) to determine if the waveform morphology is consistent with a sinus rhythm. If the AV association is stable and the R-wave morphology indicates sinus rhythm, the device concludes that the arrhythmia is an SVT and SVT therapy, such as ATP, can then be delivered. Conversely, if either the AV association is not stable and/or the R-wave morphology is not consistent with sinus rhythm, then VT is confirmed and appropriate high voltage therapy is promptly delivered. Note that, after the PVAB is reduced, if the adjusted atrial rate is then found to be greater than the ventricular rate (i.e. A>V), VT is assumed and high voltage therapy is promptly delivered. Note also that the incremental decrease in the duration of the PVAB proceeds only until a minimum PVAB duration is reached. If the adjusted atrial rate at the shortest permissible PVAB duration is still found to be less than the ventricular rate, then VT is confirmed and high voltage therapy is promptly delivered. Still further note that, if the ventricular rate was not greater than the initial atrial rate when VT was initially detected, the device preferably evaluates other branches of an overall arrhythmia diagnosis processes to further discriminate the current arrhythmia before delivering therapy.

In a second illustrative implementation of the invention, the atrial channel parameter selectively adjusted is the atrial channel sensitivity. Generally, a "high" sensitivity means that the device is capable of detecting a very small signal on a given channel. To achieve high atrial sensitivity, the actual atrial channel sensing threshold level (usually specified in terms of millivolts (mV)) is set to a low mV value. Conversely, "low" sensitivity generally means that the device can only detect a very large signal, with smaller signals ignored. To provide low atrial sensitivity, the atrial channel sensing threshold level is set to a high mV value. By way of illustration, a 0.5 mV sensing level is more sensitive (described as having a higher sensitivity) than a 2.0 mV sensing level. Herein, an "increase" in atrial channel sensitivity refers to a change toward a higher sensitivity to allow for the detection of smaller signals on the atrial channel (which involves the programming of a numerically smaller mV value.) With this in mind, atrial sensitivity is usually set sufficiently low (i.e. the atrial sensing mV level value is relatively large) to prevent noise on the atrial channel from being sensed and erroneously misidentified as atrial depolarization events (P-waves.) However, this can result in undersensing of true P-waves, especially during an SVT. That is, even if the true atrial and ventricular rates are the same, low sensitivity on the atrial channel can result in the observed atrial rate being substantially lower than the ventricular rate. As such, even if the true atrial and ventricular rates are the same indicating a likely SVT, the device might detect a ventricular rate that is greater than the observed atrial rate, triggering inappropriate VT therapy.

Accordingly, in the second illustrative implementation, upon detection of VT with V>A, the device incrementally increases atrial sensitivity (making it more sensitive so as to detect smaller atrial channel signals) to determine whether the true atrial rate is actually the same as the ventricular rate. In one example, the atrial sensitivity is incrementally increased (by decreasing the corresponding atrial sensing threshold mV level) by a programmed amount every N cardiac cycles, where N is programmable. At each adjusted level of atrial sensitivity, the device assesses the new (adjusted) atrial rate and compares it with the current ventricular rate to determine if the two rates are now the same (i.e. the device determines if the higher atrial sensitivity reveals a true atrial rate that is actually equal to the ventricular rate.)

Continuing with the second illustrative implementation, if the adjusted atrial rate at the higher sensitivity is found to be the same as the ventricular rate (i.e. V=A), then the arrhythmia might be SVT rather than VT and so the device takes steps to discriminate the two arrhythmias. As with the PVAB example discussed above, the device first assesses AV association stability and then examines R-wave morphology. If the AV association is stable and the R-wave morphology indicates sinus rhythm, the device concludes that the arrhythmia is an SVT and SVT therapy can then be delivered. Conversely, if the AV association is not stable and/or the R-wave morphology is not consistent with sinus rhythm, then VT is confirmed and appropriate high voltage therapy is delivered. Note that the incremental increase in the atrial sensitivity proceeds only until a maximum atrial sensitivity is reached (as specified by a minimum atrial sensing threshold mV value.) If the adjusted atrial rate at the greatest permissible atrial sensitivity is still not the same as the ventricular rate, then VT is confirmed and high voltage therapy is promptly delivered. This again helps ensure that there is no significant delay in the delivery of high voltage therapy in circumstances where it is needed.

In various exemplary embodiments described herein, the implantable medical device is a pacer/ICD or a CRT-D. However, the techniques of the invention can be applied to other implantable medical devices and systems, where appropriate.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Medical System

Figure 1:
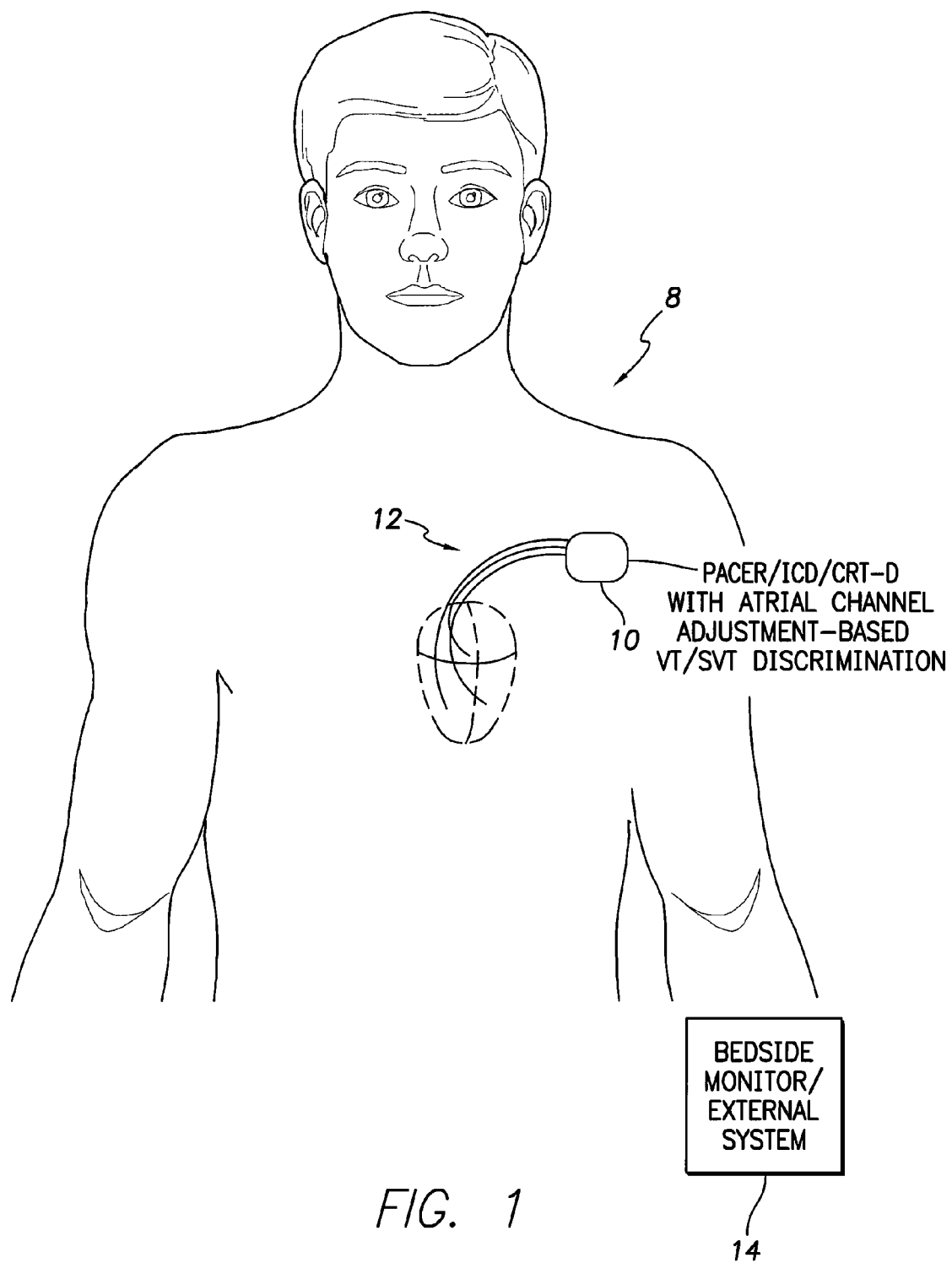
FIG. 1 illustrates pertinent components of an implantable medical system having a pacemaker, ICD or CRT-D equipped to implement atrial channel adjustment-based VT/SVT discrimination for cases where the ventricular rate exceeds the observed atrial rate.

FIG. 1 illustrates an implantable medical system 8 having a pacer/ICD or CRT-D 10 equipped with an atrial channel adjustment-based VT/SVT discrimination system for distinguishing VT from SVT within a patient in circumstances where the ventricular rate exceeds the observed atrial rate. In the following examples, a pacer/ICD is described. Other implantable cardiac rhythm management devices can instead be used, such as CRT-D devices. In the examples herein, discrimination is achieved by selectively adjusting suitable atrial channel detection parameters—such as the duration of the PVAB and the level of atrial sensitivity—to detect circumstances where a true atrial rate is being underestimated resulting in a possible false positive VT diagnosis. In some circumstances, morphological analysis of R-waves (i.e. QRS waveforms) is performed along with an analysis of AV association stability to provide further discrimination of SVT and VT. Once a determination has been made as to whether the patient is suffering from VT or SVT, pacer/ICD 10 then delivers appropriate therapy, such as atrial ATP in response to SVT or high voltage cardioversion shocks in response to VT.

Figure 5:
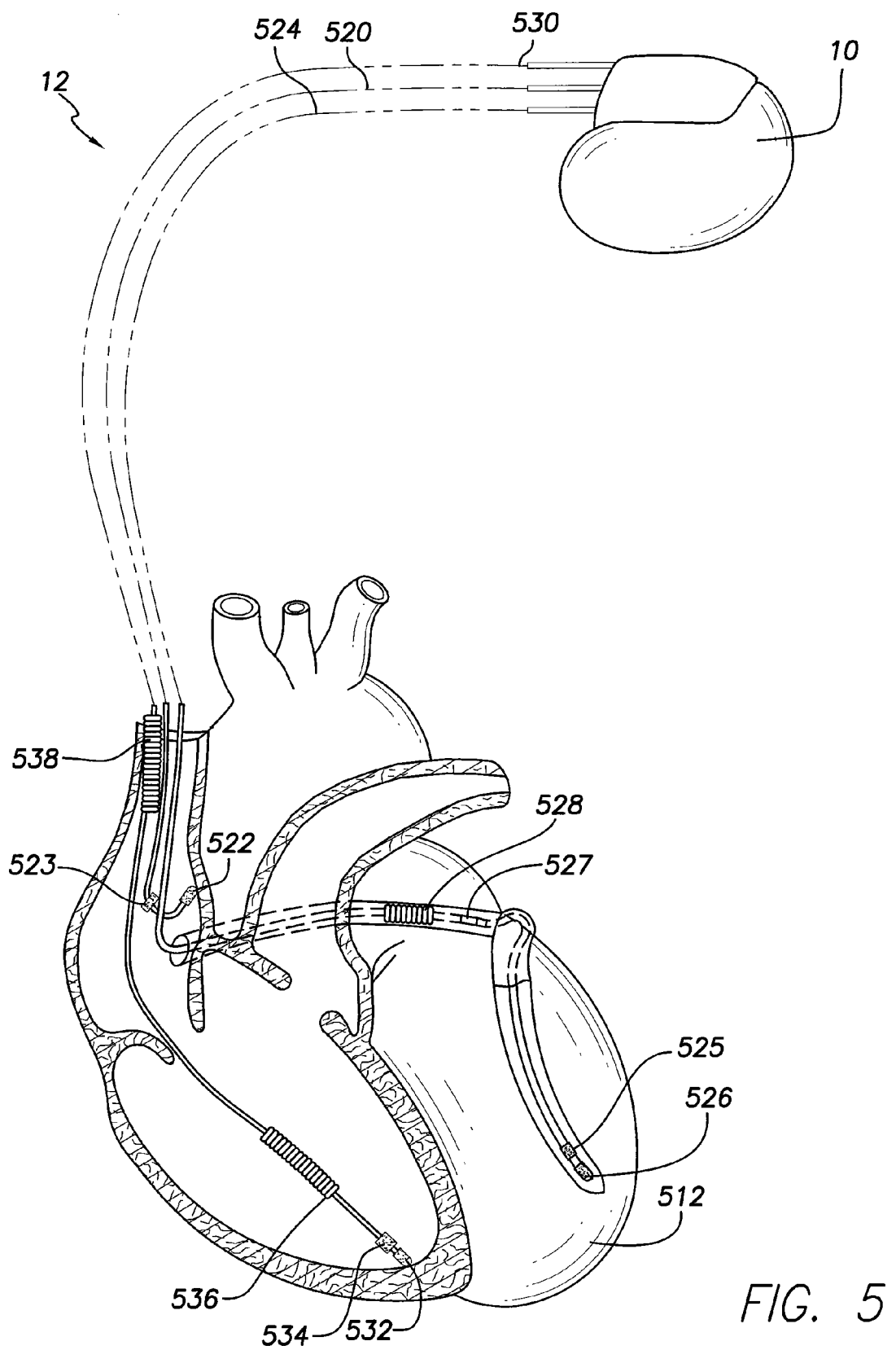
FIG. 5 is an illustration of the device of FIG. 1 along with a set of exemplary leads implanted in the heart of the patient.

The atrial and ventricular channel signals processed by the device can be intracardiac electrogram (IEGM) signals sensed via a set of pacing/sensing/shocking leads 12 implanted in the patient. In the example of FIG. 1, three leads are shown (in stylized form)—a right atrial (RA) lead, a left ventricular (LV) lead, and a right ventricular (RV) lead—for sensing the atrial and ventricular IEGM signals. A more complete and accurate illustration of a set of leads is provided in FIG. 5, described below. In particular, the LV lead is preferably implanted via the coronary sinus, as shown in FIG. 5.

In some embodiments, information pertaining to the diagnosis of the tachyarrhythmia is transmitted to an external system, such as bedside monitor 14, which generates diagnostic displays alerting the patient, family members, physician or other caregivers. The bedside monitor may be directly networked with a centralized computing system, such as the HouseCall™ system or the Merlin@home/Merlin.Net systems of St. Jude Medical, Inc., for immediately notifying a physician or other personnel of the tachyarrhythmia.

Warnings pertinent to the particular tachyarrhythmia may also be generated using the bedside monitor, a hand-held personal advisory module (PAM), not separately shown, or an internal warning device provided within the pacer/ICD. The internal warning device (which may be part of pacer/ICD) can be a vibrating device or a "tickle" voltage device that, in either case, provides perceptible stimulation to the patient to alert the patient. The bedside monitor or PAM can provide audible or visual alarm signals to alert the patient or caregiver, as well as any appropriate textual or graphic displays. In addition, diagnostic information pertaining to the tachyarrhythmia may be stored within the pacer/ICD for subsequent transmission to an external programmer (see FIG. 6) for review by a clinician during a follow-up session between patient and clinician. The clinician then prescribes any appropriate therapies, such as suitable medications. The clinician may also adjust the operation of the pacer/ICD to activate, deactivate or otherwise control any therapies automatically provided by the device.

Additionally, the pacer/ICD performs a wide variety of pacing and/or defibrillation functions, such as delivering routine pacing therapy or generating and delivering shocks in response to VF. Also, in some examples, the device is equipped to deliver CRT. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing." See, also, U.S. Patent Application No. 2008/0306567 of Park et al., entitled "System and Method for Improving CRT Response and Identifying Potential Non-Responders to CRT Therapy" and U.S. Patent Application No. 2007/0179390 of Schecter, entitled "Global Cardiac Performance."

Thus, FIG. 1 provides an overview of an implantable medical system that includes a VT/SVT discrimination system. Note that the particular shape, size and locations of the implanted components shown in FIG. 1 are merely illustrative and may not necessarily correspond to actual implant locations. As noted, preferred implant locations for the leads are more precisely illustrated and described with reference to FIG. 5.

Overview of VT/SVT Discrimination Technique

Figure 2:
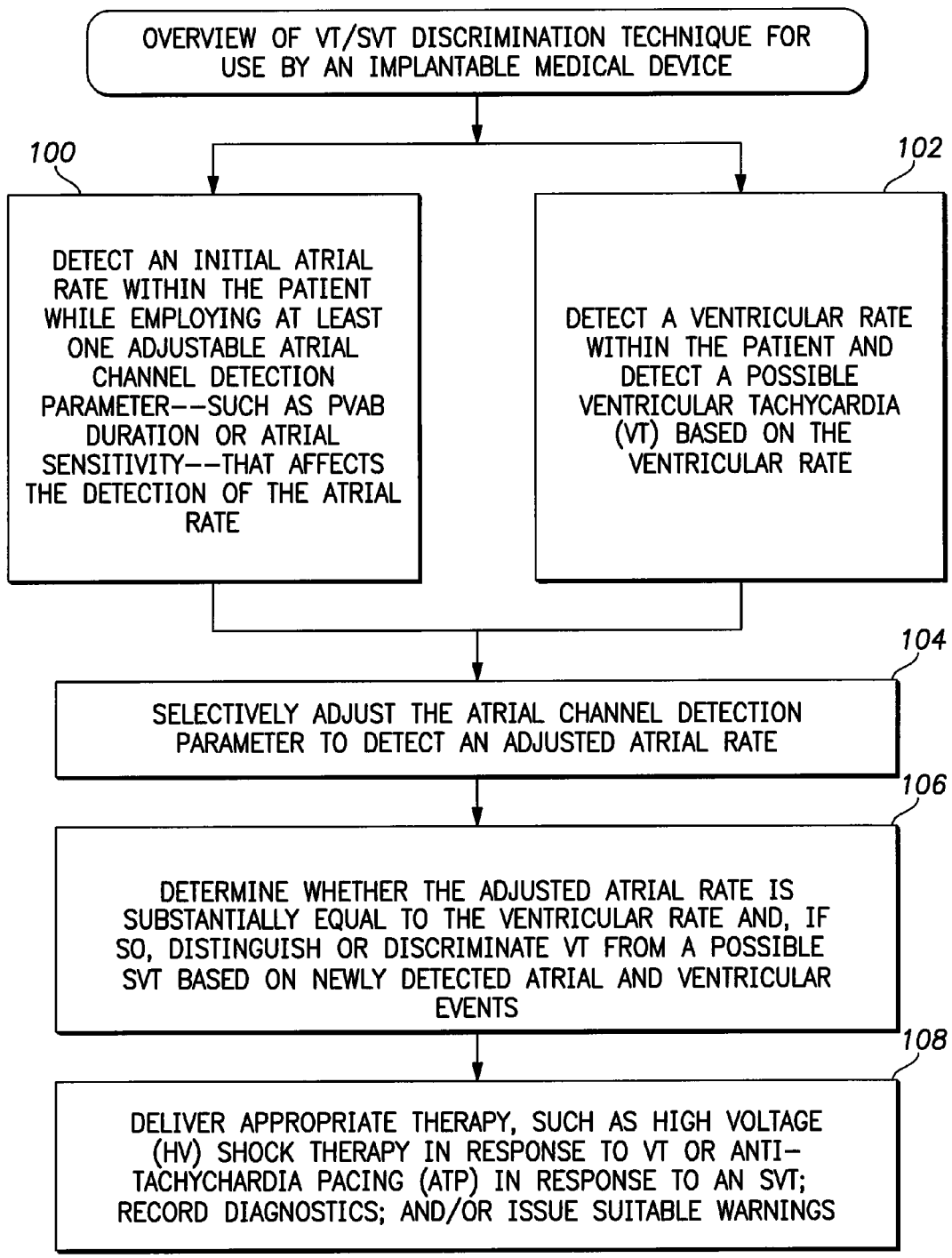
FIG. 2 is a flow chart providing an overview of the VT/SVT discrimination techniques used by the system of FIG. 1, which operate to selectively adjust atrial channel parameters such as PVAB and atrial sensitivity to distinguish VT from SVT in circumstances when the ventricular rate exceeds the observed atrial rate.

FIG. 2 provides a broad overview of the discrimination technique performed by the pacer/ICD of FIG. 1. At step 100, the pacer/ICD detects an initial atrial rate within the patient while employing at least one adjustable atrial channel detection parameter—such as PVAB duration or atrial sensitivity—that can affect the detection of the atrial rate and which, in particular, can lead to underestimation of the true atrial rate if not set properly. Concurrently, at step 102, the device detects a ventricular rate within the patient and detects a VT based on the ventricular rate, such as by detecting the ventricular rate exceeding a VT zone rate threshold (but not exceeding a higher VF zone rate threshold). At step 104, the device then selectively adjusts the atrial channel detection parameter to detect an adjusted atrial rate, wherein the adjusted rate might be higher than the initial rate if the adjustment of the atrial channel parameters reveals a true atrial rate that was previously being underestimated. Examples will be described below wherein the device operates to selectively decrease the PVAB interval or to selectively increase the atrial sensitivity. It should be understood, however, that these are merely examples. More generally, any atrial channel detection parameter that affects the detection of the atrial rate might be selectively adjusted, alone or in combination, so as to reveal the true underlying atrial rate, particularly if the parameter is one that can lead to a significant underestimation of the atrial rate if not properly set.

At step 106, the device then determines whether the adjusted atrial rate is substantially equal to the ventricular rate and, if so, the device distinguishes or discriminates VT from a possible SVT based on newly detected atrial and ventricular events. Exemplary techniques will be described in detail below that examine waveform morphology and AV association stability.

At step 108, appropriate therapy is then delivered, depending upon the capabilities of the device and device preprogramming. In response to VT, ventricular ATP or ventricular cardioversion might be delivered (i.e. one or more shocks are delivered to the ventricles.) ATP is discussed, e.g., in U.S. Pat. Nos. 6,907,286, 7,191,002 and 7,295,873. In response to SVT, atrial ATP or atrial cardioversion might be performed (i.e. one or more shocks are delivered to the atria.) See, also, therapeutic techniques described in U.S. Pat. No. 7,245,967 of Shelchuk that can be applied to supraventricular arrhythmias, depending upon the capabilities of the device. Note also that, if the ventricular rate exceeds the higher threshold indicative of VF, one or more defibrillation shocks will typically be delivered instead. (In such cases, the discrimination procedure of FIG. 1 need not be employed first. That is, upon detection of a high ventricular rate indicative of VF, defibrillation shocks are promptly delivered, as VF is life threatening.)

Additionally, or alternatively, warning signals are generated (as mentioned above) and/or diagnostics data is recorded. The diagnostic data can include information pertaining to the specific adjustments made to the atrial channel parameters, as well as the determination made by the device as to whether those adjustments revealed a true underlying atrial rate that differs from the initially-observed atrial rate. Note that, once therapy has been delivered, the atrial channel parameters can be returned to their initial values (or to other default values.)

These are just some examples of operations that can be performed by the implantable device in response to the detection and discrimination of VT, SVT or other tachyarrhythmias. Other responses might be appropriate, as well, depending upon the needs of the patient and the capabilities of the implanted device.

PVAB Adjustment Examples

Figure 3:
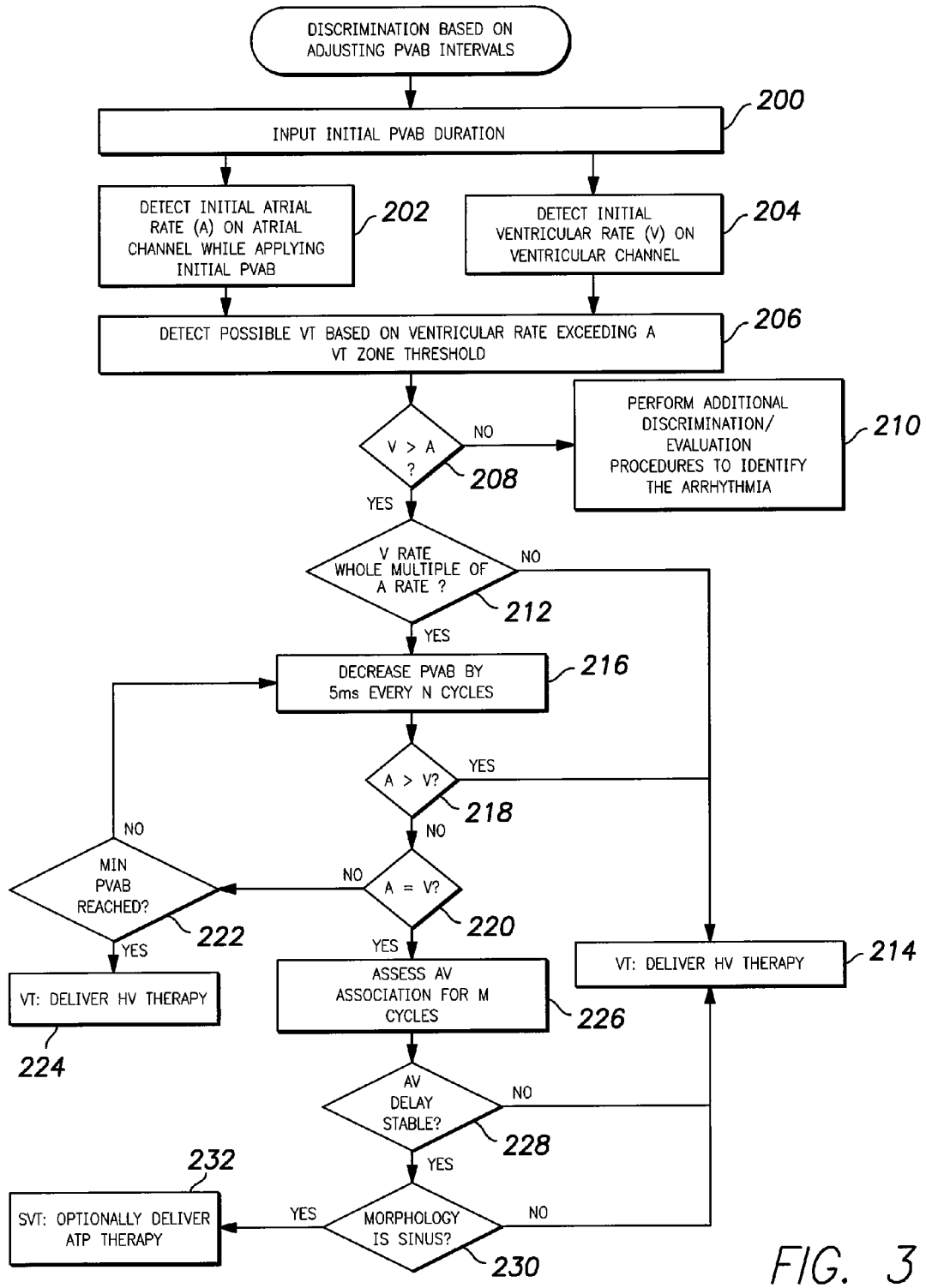
FIG. 3 is a flowchart illustrating a first exemplary discrimination technique in accordance with the general technique of FIG. 2, which selectively adjusts the PVAB interval to discriminate SVT from VT.

FIG. 3 illustrates a first exemplary implementation of the discrimination technique of FIG. 2 wherein the duration of the PVAB is selectively and incrementally reduced as a means for facilitating the discrimination of SVT from VT. Initially, at step 200, the pacer/ICD inputs or otherwise determines an initial PVAB interval for applying to one or more atrial sensing channels. A typical value for the PVAB during normal device operation is 60 ms. As noted, the PVAB interval is primarily provided to prevent the device from erroneously responding to FFRWs on the atrial channel but can interfere with the detection of high rate P-waves, particularly during SVT. As such, even if the true atrial and ventricular rates are the same (indicative of a likely SVT), the device might improperly detect a ventricular rate that is greater than the observed atrial rate, triggering inappropriate VT therapy under a "V>A" branch of an overall tachyarrhythmia detection and discrimination process employed by the device, a problem that the technique of FIG. 3 addresses.

At step 202, the device detects or tracks an initial atrial rate (herein, "A") while applying the PVAB interval. Concurrently, at step 204, the device detects or tracks an initial ventricular rate (herein, "V"). The device might also employ one or more blanking or refractory intervals on the ventricular channel, which are not pertinent to the present discussions. At step 206, the device then detects a possible VT based on the ventricular rate exceeding a VT zone threshold. In one particular example, the ventricular rate is continuously detected and compared against a VT threshold (set, e.g., to 150 beats per minute (bpm)) and a higher VF threshold (set, e.g., to 200 bpm). If the rate exceeds the higher VF threshold, VF defibrillation shocks are promptly delivered. If the rate only exceeds the lower VT threshold then a possible VT is detected.

Assuming VT is indicated, then at step 208, the device determines if the ventricular rate exceeds the atrial rate (i.e. V>A) by some nontrivial amount. If so, then the V>A branch of an overall arrhythmia detection process is entered where, as will be described shortly, steps are taken to adjust the PVAB to aid in the discrimination of SVT and VT. If V is not greater than A (i.e. V<A or V=A), then the device initiates other evaluation procedures at step 210 to discriminate the arrhythmia that are not directly pertinent to the present V>A branch discussion (but can likewise serve to discriminate VT from SVT.)

If V>A, then the device, at step 212, determines whether the ventricular rate is a whole multiple of the atrial rate. As noted, if the true (underlying) atrial and ventricular rates are the same, blanking by the PVAB can result in a detected ventricular rate that is two or three times the detected atrial rate. More specifically, for each R-wave, a corresponding P-wave might be obscured by the PVAB. Depending upon the heart rate and on the duration of the PVAB, this can cause multiple P-waves to be obscured in rapid sequence, resulting in the ventricular rate being greater than the observed atrial rate by a factor of two or three (or perhaps more). As such, if V is a whole multiple of A, this tends to indicate that the true atrial and ventricular rates are actually the same and the atrial rate is underestimated due to the PVAB. Conversely, if V>A, but V is not a whole multiple of A, this suggests that the PVAB is not the cause of the higher observed ventricular rate. Hence, if V is not a whole multiple of A, VT is indicated, at step 214, and high voltage shock therapy (or other appropriate therapies) are promptly delivered.

Assuming that V is found to be a whole multiple of A (indicating that the PVAB might be too long for the current heart rate), then the device, at step 216, incrementally decreases the PVAB by 5 ms (or by some other programmable amount in the range of 1 ms to 20 ms) for a period of N cardiac cycles (or by some other programmable amount in the range of 1 to 30 cycles.) The device then reassesses the atrial (and ventricular) rates, i.e. the device calculates new adjusted atrial (and ventricular) rates. The ventricular rate should remain unchanged but the reduced PVAB might have caused the observed atrial rate to increase by revealing additional P-waves that had previously been blanked. Indeed, the adjusted atrial rate might now exceed the ventricular rate. As such, the device then determines, at step 218, whether A>V (by some nontrivial amount.) If so, VT is again indicated, and high voltage (HV) therapy is delivered. That is, if A>V, this indicates that the arrhythmia is probably a true VT rather than an SVT, and further analysis is not warranted.

If A is not greater than V, then the device determines, at step 220, whether A and V are substantially equal. In this regard, it is not necessary for A and V to be absolutely identical; rather it is sufficient that the rates be equal within some predetermined range of values. If A and V are not substantially equal, then V is still greater than A and so a further reduction in the duration of the PVAB is warranted. Before making another reduction at step 216, the device first ensures, at step 222, that a minimum PVAB duration has not yet been reached. A suitable minimum PVAB might be programmed to 10 ms. If the minimum PVAB has already been reached, with V still greater than A, VT is diagnosed and HV therapy is delivered, at step 224. This helps ensure that VT therapy is not unduly delayed in circumstances where such therapy might be needed.

Steps 216-220 are repeated in a loop until either HV therapy is triggered at steps 214 or 224 or until A is eventually found to be substantially equal to V. As already explained, this condition indicates that the arrhythmia is likely SVT rather than VT and so high voltage therapy is not typically warranted. However, before reaching a final conclusion or diagnosis, the device performs additional steps before concluding that an SVT is indeed occurring.

Firstly, at step 226, the device assesses AV association for some programmable number of cycles "M", which might be equal to the aforementioned value N, or might be set to some other value in the range of 1 to 30 cycles. To assess AV association, the device determines whether intrinsic AV conduction delay values are substantially uniform, which would indicate that the high rate ventricular events that triggered the initial VT indication are indeed correlated with the high rate atrial events, suggesting that the arrhythmia is supraventricular in origin. Conversely, if the intrinsic AV delay values are not substantially uniform, such indicates that the high rate ventricular events are uncorrelated with the high rate atrial events, suggesting that the arrhythmia is a true VT and not a mere SVT. Otherwise conventional techniques can be used to assess the stability of the AV association, such as by calculating a standard deviation in the AV delays and comparing it to one or more suitable thresholds indicative of relative stability or uniformity. If the AV delays are not found to be stable, VT is again indicated and HV therapy delivered, at step 214.

Secondly, at step 230, the device examines the morphology of the ventricular events (i.e. R-waves) to determine whether the waveforms are consistent with a high rate sinus rhythm. If the waveforms are consistent with sinus rhythm, such indicates that the high rate ventricular events that triggered the initial VT indication are supraventricular in origin. Conversely, if the waveforms are not consistent with sinus rhythm, such indicates that the high rate ventricular events are due to a true VT and not a mere SVT. Otherwise conventional techniques can be used to assess the morphology of the R-waves, such as by template matching. If the morphology is not consistent with sinus rhythm, VT is again indicated and HV therapy delivered, at step 214.

Ultimately, if the AV association is stable and the R-wave morphology indicates sinus rhythm, the device concludes at step 232 that the arrhythmia is an SVT and so SVT therapy (such as atrial ATP) can then be delivered, depending upon the programming of the device. Although not specifically shown in the figure, after VT and SVT have been discriminated and therapy delivered, the PVAB interval can be returned to its initial or default value.

The procedure of FIG. 3 can be summarized as follows:
When a ventricular rhythm that falls in the VT zone AND the rate branch is classified as V>A AND V rate is a whole number multiple of A rate:
Decrease PVAB by 5 ms every n cycles until A rate=V rate.
Assess AV association.
Perform morphology scoring.
If the following three conditions are met:
(A=V) Rate Branch is achieved.
AV association is stable.
Morphology scores R-waves as Sinus.
Then,
Diagnose SVT & withhold VT therapy.
Otherwise,
Diagnose VT and issue HV therapy immediately.

Atrial Sensitivity Adjustment Examples

Figure 4:
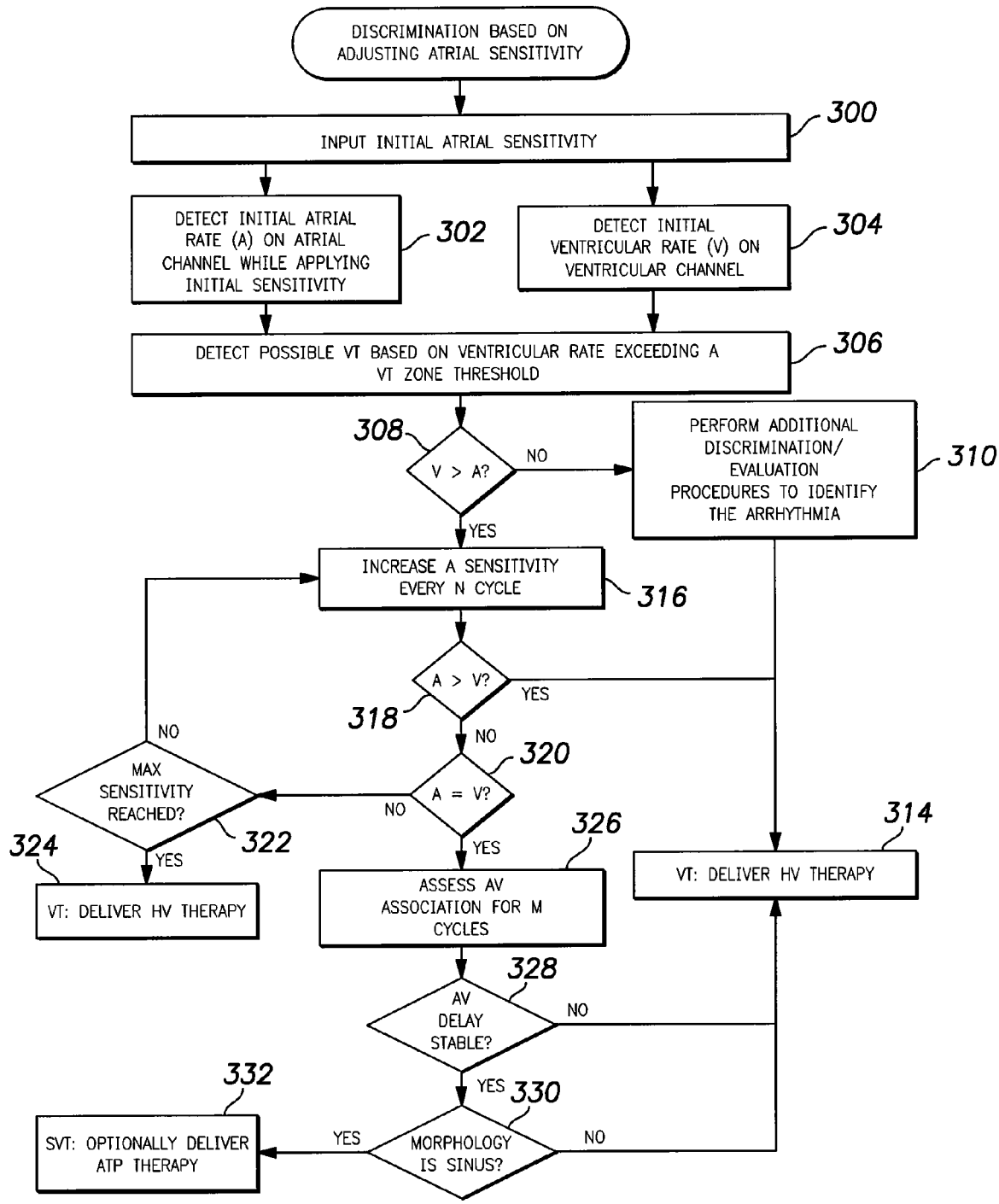
FIG. 4 is a flowchart illustrating a second exemplary discrimination technique in accordance with the general technique of FIG. 2, which selectively adjusts the atrial sensitivity to discriminate SVT from VT.

FIG. 4 illustrates a second exemplary implementation of the discrimination technique of FIG. 3 wherein the atrial sensitivity is selectively and incrementally increased as a means for facilitating the discrimination of SVT from VT. Many of the steps of FIG. 4 are similar to those of step 3 and will hence not be described in detail again. Initially, at step 300, the pacer/ICD inputs or otherwise determines an initial atrial sensitivity for applying to one or more atrial sensing channels. A typical value for the atrial sensitivity threshold level during normal device operation is 1 mV. As noted above, a relatively high sensing threshold mV level corresponds to relatively low sensitivity; whereas a relatively low sensing threshold mV level corresponds to relatively high sensitivity. As such, a 0.5 mV sensing level is more sensitive than a 2.0 mV sensing level. With this in mind, atrial sensitivity is initially set at step 300 to be sufficiently low (i.e. the atrial sensing mV level value is set relatively large) to prevent noise on the atrial channel from being sensed and erroneously misidentified as P-waves. However, this can result in undersensing of true P-waves, especially during an SVT. Hence, as with the technique of FIG. 3, even if the true atrial and ventricular rates are the same, the device might improperly detect a ventricular rate that is greater than the observed atrial rate, triggering inappropriate VT therapy under a "V>A" branch.

At step 302, the device detects or tracks the initial atrial rate (A) while applying the input atrial sensitivity interval. Concurrently, at step 304, the device detects or tracks the initial ventricular rate (V) and, at step 306, detects a possible VT. Assuming VT is indicated, then at step 308, the device determines if V>A and, if so, steps are taken to adjust the atrial sensitivity to aid in the discrimination of SVT and VT. If V A, then the device initiates other evaluation procedures at step 310 to discriminate the arrhythmia, as mentioned above. Assuming V>A, then the device, at step 316, incrementally increases the atrial sensitivity. This can be achieved be lowering the mV threshold value by, e.g., 0.25 mV (or by some other programmable amount in the range of 0.05 mV to 0.5 mV) for a period of N cardiac cycles (a programmable value that can differ from the corresponding N value used in the PVAB adjustments discussed above.) The device then calculates new adjusted atrial (and ventricular) rates. Although the ventricular rate should remain unchanged, the increased atrial sensitivity might have caused the observed atrial rate to increase by revealing additional P-waves that had previously been of too low a magnitude to be detected. The device then determines, at step 318, whether A is now greater than V and, if so, VT is again indicated and HV therapy is delivered.

At step 320, the device determines whether A and V are substantially equal. If not, then V is still greater than A and so a further incremental increase in atrial sensitivity is warranted. Before making another adjustment at step 316, the device first ensures, at step 322, that a maximum atrial sensitivity has not yet been reached. (Note that maximum sensitivity is expressed in terms of a minimum sensing threshold value in mV. A suitable minimum atrial sensing threshold might be programmed to 0.25 mV.) If the maximum atrial sensitivity has already been attained (i.e. the minimum atrial sensing threshold in mV has been reached), with V still greater than A, VT is diagnosed and HV therapy is delivered, at step 324. This helps ensure that VT therapy is not unduly delayed in circumstances where such therapy might be needed.

As with corresponding portions of FIG. 3, steps 316-320 of FIG. 4 are repeated in a loop until either HV therapy is triggered or A is eventually found to be substantially equal to V. As already explained, this condition indicates that the arrhythmia is likely SVT rather than VT and so high voltage therapy is not typically warranted. However, before reaching a final conclusion, the device performs additional discrimination steps. Briefly, at step 326, the device assesses the stability of AV association for some programmable number of cycles "M" (which could differ from the corresponding M value used in FIG. 3.) If the AV delays are relatively unstable, VT is again indicated and HV therapy delivered, at step 314. At step 330, the device examines R-wave morphology and, if it is not consistent with sinus rhythm, VT is again indicated and HV therapy delivered, at step 314. Ultimately, if AV association is stable and R-wave morphology is sinus, the device concludes at step 332 that the arrhythmia is an SVT and so SVT therapy can then be delivered, depending upon the programming of the device.

The procedure of FIG. 4 can be summarized as follows:
When a ventricular rhythm that falls in the VT zone AND the rate branch is classified as V>A rate:
Decrease atrial sensitivity until A rate=V rate.
Assess AV association.
Perform morphology scoring.
If the following three conditions are met:
(A=V) Rate Branch is achieved.
AV association is stable.
Morphology scores R-waves as Sinus.
Then,
Diagnose SVT & withhold VT therapy.
Otherwise,
Diagnose VT and issue HV therapy immediately.

Thus, FIGS. 3 and 4 illustrate exemplary techniques for adjusting certain atrial channel detection parameters (PVAB and atrial sensitivity) that affect the detection of the atrial rate for the purposes of discriminating SVT from VT in circumstances where V>A. In some implementations, it might helpful to adjust both PVAB and atrial sensitivity. In other implementations, other parameters affecting the detection of the atrial rate might be adjusted, either additionally or alternatively. Moreover, although particular iterative adjustment techniques are described herein as examples, other adjustment procedures, algorithms or techniques might instead be employed to achieve substantially the same goals.

Still further, in some implementations, it might be appropriate to employ additional or alternative VT/SVT discrimination techniques to improve overall discrimination specificity. See, for example, techniques described in: U.S. patent application Ser. No. 12/608,827, of Wang et al., filed Oct. 29, 2009, entitled "Systems and Methods for use with an Implantable Medical Device for Discriminating VT and SVT based on Ventricular Depolarization Event Timing" (A09P1056), which is assigned to the assignee of the present application.

Other discrimination techniques of possible interest are described in the following documents. Waveform discrimination techniques are described in, e.g., U.S. Pat. No. 5,273,049 to Steinhaus et al. entitled, "Detection of Cardiac Arrhythmias using Template Matching by Signature Analysis"; U.S. Pat. No. 5,240,009 to Williams, entitled "Medical Device with Morphology Discrimination"; U.S. Pat. No. 5,779,645 to Olson et al., "System and Method for Waveform Morphology Comparison," and U.S. Pat. No. 6,516,219 to Street, entitled "Arrhythmia Forecasting based on Morphology Changes in Intracardiac Electrograms." See, also, the morphology-based discrimination techniques described in U.S. patent application Ser. No. 11/674,974, filed Feb. 14, 2007, of Graumann, entitled "System and Method for Morphology-Based Arrhythmia Discrimination using Left Ventricular Signals sensed by an Implantable Medical Device." Other techniques for distinguishing VT and SVT include "sudden onset discrimination" and "PR logic discrimination." Sudden onset discrimination is discussed, e.g., in U.S. Pat. No. 6,636,764 to Fain et al., entitled "Safety Backup in Arrhythmia Discrimination Algorithm." PR logic discrimination is discussed, e.g., in U.S. Pat. No. 7,058,450 to Struble et al., entitled "Organizing Data according to Cardiac Rhythm Type."

Note also that techniques have been described with respect to examples wherein the implantable device performs all of the operations. However, some aspects of the invention might be applicable to other systems. For example, the discrimination techniques might instead be performed by an external device based on IEGM signals received from the implanted device. Exploitation of the invention within an implanted device is preferred as it allows the device itself to detect and discriminate tachyarrhythmias so as to deliver therapy promptly but implementations exploiting external devices might be useful as well, at least for diagnostic purposes.

For the sake of completeness, an exemplary pacer/ICD will now be described, which includes components for performing the functions and steps already described. As already noted, other implantable medical devices can instead be used, such as CRT-D devices.

Exemplary Pacer/ICD

Figure 6:
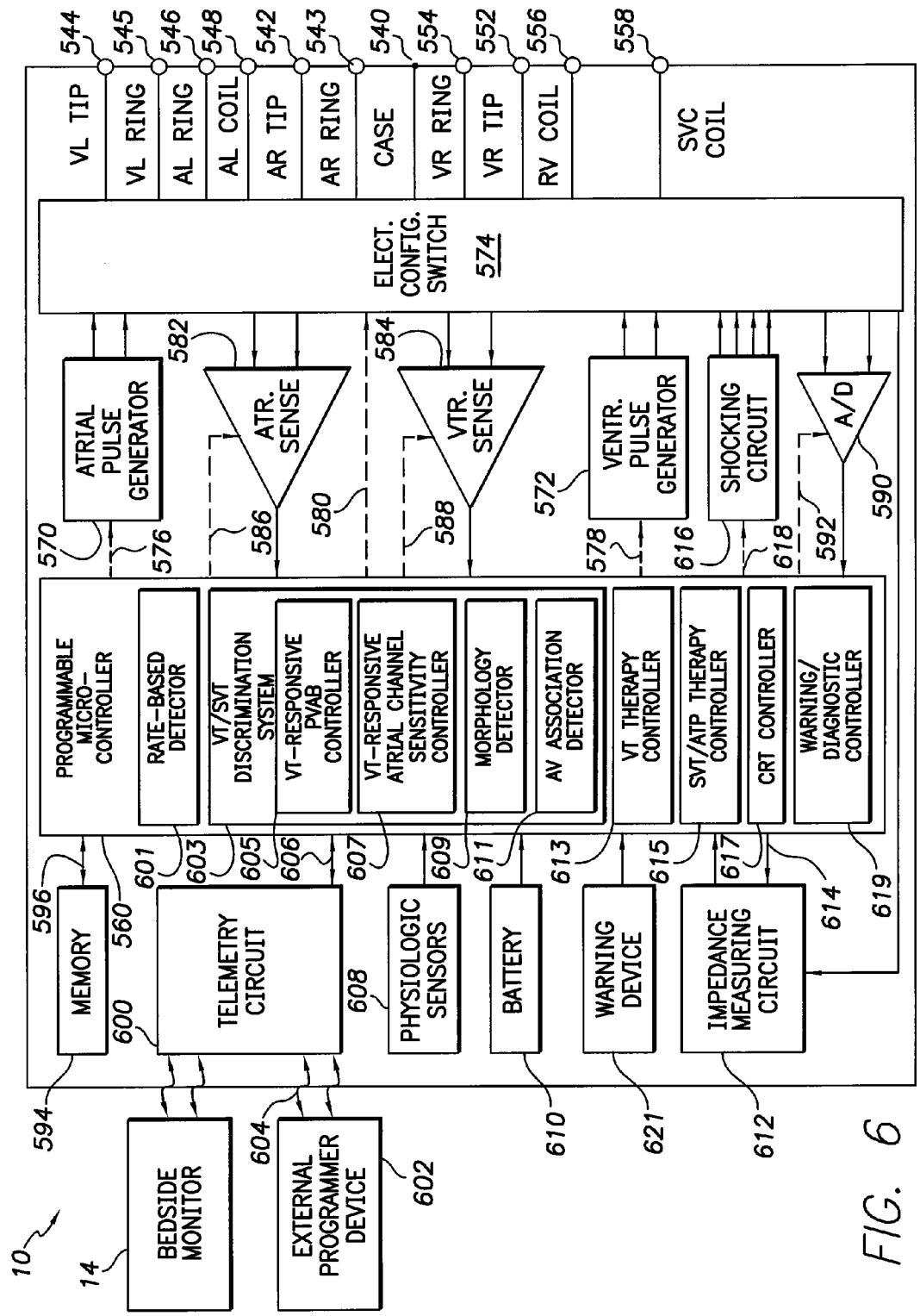
FIG. 6 is a functional block diagram of the device of FIG. 5, wherein the device is a pacer/ICD, illustrating basic circuit elements that provide cardioversion, defibrillation and/or pacing stimulation in the four chambers of the heart and particularly illustrating components for performing the various VT/SVT discrimination techniques of FIGS. 2-4.

With reference to FIGS. 5 and 6, an exemplary pacer/ICD will now be described. FIG. 5 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 10 is shown in electrical communication with a heart 512 by way of a right atrial lead 520 having an atrial tip electrode 522 and an atrial ring electrode 523 implanted in the atrial appendage. Pacer/ICD 10 is also in electrical communication with the heart by way of a right ventricular lead 530 having, in this embodiment, a ventricular tip electrode 532, a right ventricular ring electrode 534, a right ventricular (RV) coil electrode 536, and a superior vena cava (SVC) coil electrode 538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a LV/CS lead 524 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV/CS lead 524 is designed to receive atrial and ventricular cardiac signals and to deliver left ventricular pacing therapy using at least a left ventricular tip electrode 526, a left ventricular ring electrode 525, left atrial pacing therapy using at least a left atrial ring electrode 527, and shocking therapy using at least a left atrial coil electrode 528. With this configuration, biventricular pacing can be performed. Although only three leads are shown in FIG. 5, it should also be understood that additional stimulation leads (with one or more pacing, sensing and/or shocking electrodes) might be used in order to efficiently and effectively provide pacing stimulation to the left side of the heart or atrial cardioversion and/or defibrillation.

A simplified block diagram of selected internal components of pacer/ICD 10 is shown in FIG. 6. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 540 for pacer/ICD 10, shown schematically in FIG. 6, is often referred to as the "can", "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, 544, 545, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 523. To achieve left chamber sensing, pacing and shocking, the connector includes at least a left ventricular tip terminal ($V_L$ TIP) 544, a left ventricular ring terminal ($V_L$ RING) 545, a left atrial ring terminal ($A_L$ RING) 546, and a left atrial shocking terminal ($A_L$ COIL) 548, which are adapted for connection to the left ventricular ring electrode 526, the left atrial ring electrode 527, and the left atrial coil electrode 528, respectively. To support right chamber sensing, pacing and shocking, the connector further includes a right ventricular tip terminal ($V_R$ TIP) 552, a right ventricular ring terminal ($V_R$ RING) 554, a right ventricular shocking terminal ($V_R$ COIL) 556, and an SVC shocking terminal (SVC COIL) 558, which are adapted for connection to the right ventricular tip electrode 532, right ventricular ring electrode 534, the $V_R$ coil electrode 536, and the SVC coil electrode 538, respectively.

At the core of pacer/ICD 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry.

Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 6, an atrial pulse generator 570 and a ventricular pulse generator 572 generate pacing stimulation pulses for delivery by the right atrial lead 520, the right ventricular lead 530, and/or the LV/CS lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses. The microcontroller 560 further includes timing control circuitry (not separately shown) used to control the timing of such stimulation pulses (e.g., pacing rate, atrioventricular (A-V) delay, atrial interconduction (inter-atrial or A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art.

Atrial sensing circuits 582 and ventricular sensing circuits 584 may also be selectively coupled to the right atrial lead 520, LV/CS lead 524, and the right ventricular lead 530, through the switch 574 for detecting the presence of cardiac activity in each of the four chambers of the heart. As such, these components, either alone or in combination with other device components, provide: an atrial rate detector operative to detect an initial atrial rate within the patient while employing at least one adjustable atrial channel detection parameter that affects the detection of the atrial rate; and a ventricular rate detector operative to detect a ventricular rate within the patient. The atrial and ventricular sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, pacer/ICD 10 utilizes the atrial and ventricular sensing circuits, 582 and 584, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate ventricular tachycardia, high rate ventricular tachycardia, and fibrillation rate zones) and various other characteristics (e.g., sudden onset, stability, physiologic sensors, and morphology, etc.) in order to determine the type of remedial therapy that is needed (e.g., bradycardia pacing, ATP, cardioversion shocks or defibrillation shocks).

Cardiac signals are also applied to the inputs of an analog-to-digital (ND) data acquisition system 590. The data acquisition system 590 is configured to acquire intracardiac electrogram signals, convert the raw analog data into a digital signal, and store the digital signals for later processing and/or telemetric transmission to an external device 602. The data acquisition system 590 is coupled to the right atrial lead 520, the LV/CS lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 594 through a telemetry circuit 600 in telemetric communication with the external device 602, such as a programmer, transtelephonic transceiver or a diagnostic system analyzer, or with a beside monitor 14. The telemetry circuit 600 is activated by the microcontroller by a control signal 606. The telemetry circuit 600 advantageously allows intracardiac electrograms and status information relating to the operation of pacer/ICD 10 (as contained in the microcontroller 560 or memory 594) to be sent to the external device 602 through an established communication link 604. Pacer/ICD 10 further includes an accelerometer or other physiologic sensor 608, commonly referred to as a "rate-responsive" sensor because it is typically used to adjust pacing stimulation rate according to the exercise state of the patient. However, the physiological sensor 608 may further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, A-V delay, V-V delay, etc.) at which the atrial and ventricular pulse generators, 570 and 572, generate stimulation pulses. While shown as being included within pacer/ICD 10, it is to be understood that the physiologic sensor 608 may also be external to pacer/ICD 10, yet still be implanted within or carried by the patient.

A common type of rate responsive sensor is an activity sensor incorporating an accelerometer or a piezoelectric crystal, which is mounted within the housing 540 of pacer/ICD 10. Other types of physiologic sensors are also known, for example, sensors that sense the oxygen content of blood, respiration rate and/or minute ventilation, pH of blood, ventricular gradient, PPG etc. Multiple sensors may be provided.

The pacer/ICD additionally includes a battery 610, which provides operating power to all of the circuits shown in FIG. 6. The battery 610 may vary depending on the capabilities of pacer/ICD 10. If the system only provides low voltage therapy, a lithium iodine or lithium copper fluoride cell may be utilized. For pacer/ICD 10, which employs shocking therapy, the battery 610 must be capable of operating at low current drains for long periods, and then be capable of providing high-current pulses (for capacitor charging) when the patient requires a shock pulse. The battery 610 must also have a predictable discharge characteristic so that elective replacement time can be detected. Accordingly, pacer/ICD 10 is preferably capable of high voltage therapy and appropriate batteries.

As further shown in FIG. 6, pacer/ICD 10 is shown as having an impedance measuring circuit 612 which is enabled by the microcontroller 560 via a control signal 614. Thoracic impedance may be detected for use in tracking thoracic respiratory oscillations; lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 612 is advantageously coupled to the switch 574 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 560 further controls a shocking circuit 516 by way of a control signal 618. The shocking circuit 516 generates shocking pulses of low (up to 0.5 joules), moderate (0.5-10 joules) or high energy (11 to 40 joules or more), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with a VF event and/or pertaining to the treatment of tachycardia. Defibrillation shocks are generally of moderate to high energy level (i.e., corresponding to thresholds in the range of 5-40 joules or more), delivered asynchronously (since VF events may be too disorganized), and pertaining exclusively to the treatment of fibrillation. Accordingly, the microcontroller 560 is capable of controlling the synchronous or asynchronous delivery of the shocking pulses.

Insofar as VT/SVT discrimination is concerned, the microcontroller includes a rate-based VT/SVT detector 601 operative to detect a tachyarrhythmia affecting the ventricles based on the ventricular rate by, e.g., using one or more rate thresholds, such as a VT rate zone threshold. (A separate detector may be provided for detecting VF.) A VT/SVT discrimination system 603 is operative to discriminate or distinguish VT from SVT in accordance with the techniques generally described above, especially in cases where V>A. The VT/SVT discrimination system includes a VT-responsive PVAB controller 605 operative to selectively adjust the PVAB to reveal P-waves that might previously have been blanked. A VT-responsive atrial channel sensitivity controller 607 is operative to selectively adjust the atrial sensitivity to reveal P-waves that might have been undersensed. Individually or collectively, controllers 605 and 607 provide a VT-responsive atrial channel controller operative to selectively adjust atrial channel detection parameter(s) to, e.g., detect an adjusted atrial rate. A morphology detector 609 is operative to examine the morphology of R-waves to determine whether the R-waves are consistent with sinus rhythm, as discussed above. An AV association detector 611 is operative to assess the stability of AV association, as discussed above. Individually or collectively, the various components of the VT/SVT discrimination system provide a discriminator operative to determine whether an adjusted atrial rate is substantially equal to a detected ventricular rate and, if so, to distinguish VT from SVT based on newly detected atrial and ventricular events.

Additionally, the microcontroller provides a VT therapy controller 613 is operative to control delivery of therapy in response to VT, such as by controlling the delivery of high voltage shocks via shocking circuit 616. An SVT/ATP therapy controller 615 is operative to control delivery of therapy in response to SVT, such as by controlling the delivery of ATP via the various pacing pulse generators, already described. A CRT controller 617 is operative to control the delivery of CRT, enabling the device to function as a CRT device, as well as a pacer/ICD.

A warning/diagnostics controller 619 controls the generation of warning signals and diagnostic data based on the results of the operation of the other units of the microcontroller, such as the generation of warning signals for relaying to bedside monitor 14 to notify the patient and/or physician of the onset, duration and type of various tachyarrhythmias. Warning signals may be delivered to the patient via a warning device 621, which may be, e.g., a vibrational warning device or a device that provide a perceptible "tickle" voltage.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, as application specific integrated circuits (ASICs) or the like.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use by an implantable medical device for implant within a patient, the method comprising:
   detecting an initial atrial rate within the patient while using at least one adjustable atrial channel detection parameter that affects the detection of the atrial rate;
   detecting a ventricular rate within the patient and detecting a possible ventricular tachycardia (VT) based on the ventricular rate;
   selectively adjusting the atrial channel detection parameter to detect an adjusted atrial rate; and
   determining whether the adjusted atrial rate is substantially equal to the ventricular rate and, if so, distinguishing VT from a possible supraventricular tachycardia (SVT) based on newly detected atrial and ventricular events.

2. The method of claim 1 wherein selectively adjusting the atrial channel detection parameter is only performed if the ventricular rate exceeds the initial atrial rate.

3. The method of claim 2 wherein the atrial channel detection parameter is a post-ventricular atrial blanking interval (PVAB) applied to an atrial sensing channel and wherein the step of selectively adjusting the atrial channel detection parameter is performed to selectively shorten the PVAB.

4. The method of claim 3 wherein selectively shortening the PVAB is performed only if the ventricular rate is a whole multiple of the initial atrial rate.

5. The method of claim 4 wherein, if the ventricular rate is not a whole multiple of the initial atrial rate, VT therapy is delivered to the patient without shortening the PVAB.

6. The method of claim 3 wherein distinguishing VT from a possible SVT based on newly detected atrial and ventricular events while using the shortened PVAB includes:
   assessing a degree of atrioventricular AV association between the newly detected atrial and ventricular events to determine whether the AV association is stable;
   assessing a morphology of the newly detected ventricular events to determine whether the morphology indicates sinus rhythm;
   identifying the tachycardia as SVT if the AV association is stable and the ventricular morphology indicates sinus rhythm; and
   identifying the tachycardia as VT otherwise.

7. The method of claim 3 wherein the PVAB is selectively shortened to be no less than a predetermined minimum PVAB and, if the PVAB reaches the minimum PVAB without the adjusted atrial rate becoming substantially equal to the ventricular rate, VT is confirmed and VT therapy is delivered.

8. The method of claim 2 wherein the atrial channel detection parameter is a sensitivity applied to an atrial sensing channel.

9. The method of claim 8 wherein selectively adjusting the atrial channel detection parameter is performed to selectively increase the atrial sensitivity.

10. The method of claim 8 wherein distinguishing VT from a possible SVT based on newly detected atrial and ventricular events while using the increased sensitivity includes:
    assessing a degree of atrioventricular AV association between the newly detected atrial and ventricular events to determine whether the AV association is stable;
    assessing a morphology of the newly detected ventricular events to determine whether the morphology indicates sinus rhythm;
    identifying the tachycardia as SVT if the AV association is stable and the ventricular morphology indicates sinus rhythm; and
    identifying the tachycardia as VT otherwise.

11. The method of claim 9 wherein the atrial channel sensitivity is selectively increased to be no greater than a predetermined maximum sensitivity level and, if the atrial channel sensitivity reaches the maximum sensitivity level without the adjusted atrial rate becoming substantially equal to the ventricular rate, VT is confirmed and VT therapy is delivered.

12. The method of claim 1 wherein if the ventricular rate does not exceed the initial atrial rate upon initial detection of a possible VT, then VT further discrimination steps are performed for distinguishing VT from SVT before therapy is delivered.

13. The method of claim 1 wherein detecting a possible VT based on the ventricular rate is performed based on a VT rate zone threshold.

14. The method of claim 1 further including delivering therapy in response to a confirmation of the detection of VT.

15. The method of claim 14 wherein the therapy includes high voltage shocks.

16. The method of claim 1 further including recording diagnostic information in response to distinguishing VT from a possible SVT representative of the arrhythmia.

17. A system for use by an implantable medical device for implant within a patient, the system comprising:

means for detecting an initial atrial rate within the patient while using at least one adjustable atrial channel detection parameter that affects the detection of the atrial rate;

means for detecting a ventricular rate within the patient and means for detecting a possible ventricular tachycardia (VT) based on the ventricular rate;

means for selectively adjusting the atrial channel detection parameter to detect an adjusted atrial rate; and means for determining whether the adjusted atrial rate is substantially equal to the ventricular rate and, if so, for distinguishing VT from a possible supraventricular tachycardia (SVT) based on newly detected atrial and ventricular events.

* * * * *